United States Patent [19]

Kolts et al.

[11] Patent Number: 4,620,052

[45] Date of Patent: Oct. 28, 1986

[54] DEHYDROGENATION AND CRACKING OF $C_3$ AND $C_4$ HYDROCARBONS

[75] Inventors: John H. Kolts, Ochelata; Gary A. Delzer, Bartlesville, both of Okla.

[73] Assignee: Phillips Petroleum Company, Bartlesville, Okla.

[21] Appl. No.: 758,936

[22] Filed: Jul. 25, 1985

[51] Int. Cl.[4] .............................................. C07C 5/333
[52] U.S. Cl. .................................. 585/663; 585/661; 585/653; 585/651
[58] Field of Search ................ 585/651, 653, 661, 663

[56] References Cited

U.S. PATENT DOCUMENTS

| | | | |
|---|---|---|---|
| 2,098,959 | 11/1937 | Frey et al. | 585/663 |
| 2,122,787 | 7/1938 | Tropsch | 585/663 |
| 2,415,477 | 2/1947 | Folkins et al. | 585/651 |
| 2,422,172 | 6/1945 | Smith et al. | 585/663 |
| 3,644,557 | 2/1972 | Senes et al. | 585/651 |
| 3,751,514 | 8/1973 | Hoppstock et al. | 585/653 |
| 3,751,516 | 8/1973 | Frech et al. | 585/653 |
| 3,766,278 | 10/1973 | Bogart et al. | 585/651 |
| 4,087,350 | 5/1978 | Kolombos et al. | 585/653 |
| 4,093,536 | 6/1978 | Heckelsberg | 585/653 |
| 4,152,300 | 5/1979 | Riesser | 502/324 |
| 4,159,970 | 7/1979 | Heckelsberg | 502/324 |
| 4,172,854 | 10/1979 | Ellis et al. | 585/663 |
| 4,471,151 | 9/1984 | Kolts | 585/651 |

FOREIGN PATENT DOCUMENTS

| | | | |
|---|---|---|---|
| 0800634 | 12/1968 | Canada | 585/663 |
| 47-42703 | 12/1972 | Japan | 585/653 |
| 1159067 | 7/1969 | United Kingdom | 585/663 |
| 1185127 | 3/1970 | United Kingdom | 585/663 |
| 1306087 | 2/1973 | United Kingdom | 585/651 |
| 0422165 | 8/1974 | U.S.S.R. | 585/651 |
| 0626111 | 9/1978 | U.S.S.R. | 585/651 |

Primary Examiner—John Doll
Assistant Examiner—Lance Johnson
Attorney, Agent, or Firm—C. F. Steininger

[57] ABSTRACT

Novel compositions of matter include: mixed oxides of (a) at least one oxide of chromium, at least one oxide of manganese and at least one oxide of magnesium, Lanthanum Series metals, preferably lanthanum and cerium, and/or niobium; (b) at least one oxide of chromium, at least one oxide of calcium, strontium, tin and/or antimony, at least one oxide of manganese and at least one oxide of magnesium, Lanthanum Series metals and/or niobium; (c) at least one oxide of chromium, at least one oxide of iron and at least one oxide of magnesium, Lanthanum Series metals and/or niobium; and (d) at least one oxide of chromium, at least one oxide of iron, at least one oxide of manganese and at least one oxide of magnesium, Lanthanum Series metals and/or niobium. These compositions are particularly effective as catalyst compositions for the conversion of $C_3$ and $C_4$ hydrocarbons to less saturated hydrocarbons, with high selectivities to ethylene and ethane and particularly ethylene, and the addition of the chromium significantly extends the activity of the catalyst for such selective conversion before regeneration is necessary. A method of converting $C_3$ and $C_4$ hydrocarbons to less saturated hydrocarbons, and selectively to ethylene and ethane and particularly ethylene, is also disclosed. Carrying out the process in the presence of steam is essential to the process when the catalyst contains iron and is optional when the catalyst does not contain iron. Limiting the amount of bound or fixed sulfur in the catalyst also improves the catalyst.

30 Claims, No Drawings

DEHYDROGENATION AND CRACKING OF $C_3$ AND $C_4$ HYDROCARBONS

The present invention relates to improved compositions of matter. In a more specific aspect, the present invention relates to improved catalysts for the conversion of $C_3$ and $C_4$ hydrocarbons to less saturated hydrocarbons. In a more specific aspect, the present invention relates to improved catalysts for the conversion of $C_3$ and $C_4$ alkanes to less saturated hydrocarbons, particularly ethylene and propylene and preferably ethylene.

BACKGROUND OF THE INVENTION

Olefins, such as ethylene and propylene, have become major feedstocks in the organic chemical and petrochemical industries. Of these, ethylene is by far the most important chemical feedstock, since the requirements for ethylene feedstocks are about double those for propylene feedstocks. Consequently, improved methods for the conversion of less valuable hydrocarbons to ethylene and propylene, and particularly to ethylene, are highly desirable.

Numerous suggestions have been made for the production of ethylene and propylene, particularly ethylene, from various feedstocks and by a wide variety of processes.

At the present time, ethylene is produced almost exclusively by dehydrogenation or thermal cracking of ethane and propane, naphtha and, in some instances, gas oils. About 75% of the ethylene currently produced in the United States is produced by steam cracking of ethane and higher normally gaseous hydrocarbon components of natural gas, since natural gas contains from about 5 vol.% to about 60 vol.% of hydrocarbons other than methane. However, in most instances, the content of ethane and higher normally gaseous hydrocarbon materials in natural gas is less than about 25% and usually less than about 15%. Consequently, these limited quantities of feedstocks, which are available for the production of ethylene and propylene, and particularly etheylene, must be utilized efficiently. Unfortunately, these processes result in low conversions to olefins and selectivity to ethylene, as opposed to propylene, is poor. In addition, relatively severe conditions, particularly temperatures in excess of about 1000° C., are required and such processes are highly energy intensive.

In order to reduce the severity of the conditions and, more importantly, to improve the conversion of normally gaseous feedstocks to ethylene and propylene and selectivity to ethylene, numerous processes involving the use of solid contact materials have been proposed. Some of these proposals utilize inert solid contact materials to improve contact between the feed hydrocarbons and steam and also to maintain a more even temperature throughout the zone of reaction. In other instances, the solid contact material is catalytic in nature. Such use as solid contact materials, particularly catalysts, have resulted in modest improvements in conversion to ethylene and propylene but the selectivity to ethylene is improved very little. It is, therefore, highly desirable that improved catalytic processes be developed, particularly processes which increase the selectivity to ethylene, as opposed to propylene. However, little is understood concerning the manner in which such catalysts function, why certain components are effective while similar components are ineffective, or why certain combinations of components are effective and other combinations are not. Obviously, a number of theories have been proposed by workers of the art, but this only adds to the confusion, since it appears that each theory explains why a particular catalytic material works well, but does not explain why similar catalytic materials do not work and why other dissimilar materials are effective. As a result, the art of catalytic conversion of hydrocarbons to olefins remains highly unpredictable.

SUMMARY OF THE INVENTION

It is therefore an object of the present invention to provide improved compositions of matter and methods of utilizing the same, which overcome the above and other disadvantages of the prior art. Another object of the present invention is to provide improved compositions of matter. Still another object of the present invention is to provide improved catalytic compositions for the conversion of $C_3$ and $C_4$ hydrocarbons to less saturated hydrocarbons. Another and further object of the present invention is to provide an improved method for the conversion of $C_3$ and $C_4$ hydrocarbons to less saturated hydrocarbons, in the presence of steam. Yet another object of the present invention is to provide an improved process for the conversion of $C_3$ and $C_4$ hydrocarbons to less saturated hydrocarbons, in the presence of steam, to selectively produce ethylene, ethane and propylene, and particularly ethylene. A further object of the present invention is to provide an improved catalytic material for the conversion of $C_3$ and $C_4$ hydrocarbons to less saturated hydrocarbons, which has an improved effective life, before regeneration is necessary, particularly for the production of ethylene, ethane and propylene, and more particularly ethylene.

The present invention provides improved compositions of matter, including: (a) at least one oxide of chromium, at least one oxide of manganese and at least one oxide of magnesium, Lanthanum Series metals, particularly lanthanum and cerium, and/or niobium; (b) at least one oxide of chromium, at least one oxide of calcium, strontium, barium, tin and/or antimony, particularly calcium, at least one oxide of manganese and at least one oxide of magnesium, Lanthanum Series metals and/or niobium; (c) at least one oxide of chromium, at least one oxide of iron and at least one oxide of magnesium, Lanthanum Series metals and/or niobium; and (d) at least one oxide of chromium, at least one oxide of iron, at least one oxide of manganese and at least one oxide of magnesium, Lanthanum Series metals and/or niobium. These compositions have been found to be highly effective catalytic compositions for the conversion of feed hydrocarbons comprising at least one of $C_3$ and $C_4$ hydrocarbons to less saturated hydrocarbons. A method of converting feed hydrocarbons comprising $C_3$ and $C_4$ hydrocarbons to less saturated hydrocarbons, particularly ethylene and propylene and preferably ethylene, in which the feed hydrocarbons are contacted with one of the above-mentioned catalytic compositions under conditions sufficient to convert the feed hydrocarbons to less saturated product hydrocarbons, is included. When the catalyst compositions contain iron, it is essential that the process be carried out in the presence of steam in order to maintain the activity of the catalyst for a viable period of time for the production of olefins and particularly ethylene and, when the catalyst is free of iron, it is optional to carry out the process in the presence of steam. The effectiveness of the catalytic compositions is also improved by limiting the sulfur content thereof.

DETAILED DESCRIPTION OF THE INVENTION

The hydrocarbon feed components, in accordance with the present invention, can include any normally gaseous hydrocarbon stream containing significant amounts of $C_3$ and $C_4$ hydrocarbons, particularly propane and n-butane, with n-butane being preferred. The presence of other normally gaseous components or even normally liquid components, which vaporize at operating conditions, are not detrimental to the process. For example, it has been found that if isobutane is utilized, in accordance with the present invention, the catalysts of the present invention shift the product stream from isobutene to propylene and, therefore, one of the desired products of the present invention is produced. On the other hand, it has been found that the catalytic process of the present invention is generally ineffective, as compared with a strictly thermal process, in improving the conversion of ethane to ethylene. However, the presence of ethane in feed hydrocarbons, obviously, is not detrimental. Components other than hydrocarbons are also not detrimental. The primary criteria in all cases is the cost or difficulty of separating inert materials or the products of components other than $C_3$ and $C_4$ hydrocarbons from the desired ethylene and propylene and whether such separation is less costly and/or less difficult before or after conduct of the process of the present invention. Suitable feedstocks for the process of the present invention can be obtained from any source, including natural gas, refinery off-gases and the like. However, the most convenient and abundant source is $C_3$ and $C_4$ hydrocarbon streams recovered during the processing of a natural gas to produce a pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6$+hydrocarbons or natural gasoline), then $C_5$, followed by $C_4$, then $C_3$ and, finally, $C_2$ hydrocarbons, by cooling to successively lower temperatures with the separation or fractionation of the condensed liquid from uncondensed vapor between cooling stages. Thus, individual streams predominating in an individual hydrocarbon, such as $C_5$, $C_4$, $C_3$ and $C_2$, can be obtained or streams predominating in combinations of the individual hydrocarbons can be recovered. Accordingly, the thus separated propane stream or the thus separated butanes stream can be utilized as a feed hydrocarbon for the present invention, or a stream predominating in a mixture of propane and butanes can be utilized. Obviously, the latter would eliminate the necessity of one stage of cooling and separation in a natural gas processing system.

The compositions of matter of the present invention include one of the following groups of mixed oxides:

(a) at least one oxide of chromium, at least one oxide of manganese, at least one oxide of magnesium, Lanthanum Series metals and/or niobium. When Lanthanum Series metals are utilized the metal is preferably selected from the group consisting of lanthanum and cerium.

(b) at least one oxide of chromium, at least one oxide of calcium, strontium, barium, tin and/or antimony, at least one oxide of manganese and at least one oxide of magnesium, Lanthanum Series metals and/or niobium.

In the above compositions, at least one Group IIA metal selected from the group consisting of calcium, strontium and barium are preferred and particularly calcium. Lanthanum Series metals are preferably selected from the group consisting of lanthanum and cerium.

(c) at least one oxide of chromium, at least one oxide of iron and at least one oxide of magnesium, Lanthanum Series metals and/or niobium. In this composition, also, the Lanthanum Series metals are preferably selected from the group consisting of lanthanum and cerium.

(d) at least one oxide of chromium, at least one oxide of iron, at least one oxide of manganese, and at least one oxide of magnesium, Lanthanum Series metals and/or niobium.

The Lanthanum Series metals are preferably selected from the group consisting of lanthanum and cerium.

The exact nature of these compositions is not known, except to the extent that it is believed that all components are present in their oxide form. Consequently, the metals may be present as single electrically balanced oxides or mixtures of oxides and possibly mixtures of electrically balanced oxides and partial oxides. For this reason, the content of the components which are present in the compositions in minor amounts are expressed in terms of the weight percent of elemental metal based on the total weight of the composition. Also, from time to time, herein, the oxides of magnesium, Lanthanum Series metals and niobium are referred to as bases or base materials, whereas the remaining components are referred to as active components or promoters. Such reference is simply a matter of convenience, since the oxides of magnesium, Lanthanum Series metals and niobium are generally present in major amounts, whereas the remaining components are present in minor amounts. Accordingly, it is to be understood that such reference is not meant to categorize the components. As will appear hereinafter, all recited components are necessary and all are catalytically active in a process of the present invention.

As previously indicated, the above-mentioned compositions of matter have been found to be particularly effective as catalytic compositions for the conversion of $C_3$ and $C_4$ hydrocarbons to less saturated hydrocarbons. Accordingly, for such use, the compositions will generally contain a major proportion of the oxides of magnesium, Lanthanum Series metals and/or niobium and minor amounts of the remaining components. The remaining components are preferably each present in amounts between about 0.1 to about 30 wt. %, expressed in terms of the elemental metal based to the total weight of the composition, and preferably between about 0.5 and about 15 wt. %. The above-mentioned catalyst compositions, without the chromium oxide, have been found to be effective for the conversion of $C_3$ and/or $C_4$ hydrocarbons to ethylene and propylene and selectively to ethylene. However, it has been discovered, in accordance with the present invention, that the addition of the chromium oxide not only extends the active life of the catalysts for the selective production of ethylene and ethane, as opposed to propylene, before regeneration of the catalyst is necessary, but also increases the selectivity to ethylene and ethane, the latter of which can be more readily converted to ethylene. It has also been found highly desirable to limit the amount of "bound" or "fixed" sulfur in the components used to prepare the catalyst compositions of the present invention to less than about 0.2 wt. %. It appears that the presence of such bound or fixed sulfur in a catalytic material tends to inhibit the selectivity of the catalyst for the production of $C_2$ hydrocarbons. Such sulfur is referred to as "bound" or "fixed" sulfur, since it does not appear to be converted to hydrogen sulfide or to be otherwise lost during the hydrocarbon conversion process or the regeneration step and is probably present in sulfate form.

The method of preparation of the catalyst compositions of the present invention does not appear to be critical, so long as the desired final compositions of the component metal ozides is obtained. Suitable methods of preparation include slurry blending, solution blending, dry blending, impregnation and co-precipitation, all of which are well known to those skilled in the art. A convenient method is to add metal solids, such as MgO or $Mg(OH)_2$, of the base material to a blending apparatus along with an aqueous solution of a metal salt, such as manganese nitrate, ferric nitrate, etc., of the active components and/or promoters and mix for several minutes, for example, 2-5 minutes, to form a thick slurry. In the interest of economy, excess water should be avoided. The resulting slurry is then dried in air by conventional means, at about 100° C. to 150° C., calcined for about four hours, at about 750° C. to 800° C., and then ground, sieved and, optionally, pelleted or otherwise sized by means well known in the art. It is also convenient to form combinations of bases and other components, usually the active components, by slurrying and impregnate the thus formed mixture with other components.

When utilizing the above-mentioned catalyst compositions, containing iron oxide, it has been found, in accordance with another aspect of the present invention, that steam is essential to the conduct of the process. Specifically, the presence of steam, during the conduct of the conversion of $C_3$ and $C_4$ hydrocarbons, greatly extends the active life of the catalyst and it has been found that, without steam, over an extended period of time, the iron oxide reduces to metallic iron, which is ineffective in the process. On the other hand, when a catalyst composition does not contain iron, it may be utilized without steam being present. However, it is preferred that steam be utilized in these cases also, since it has been found to extend the life of the catalyst before regeneration is necessary.

The process of the present invention can be carried out in fixed, moving, fluidized, ebulating or entrained bed reactors. For experimental purposes and, obviously, to permit accurate measurement and precise control of the process variables, the runs hereinafter set forth in the examples were conducted in a fixed bed reactor.

During operation, in accordance with the present invention, it has been found that small amounts of the feedstock are converted to coke, which is then deposited upon the catalyst and contributes to a decline in the catalyst activity, particularly the selectivity to ethylene. Accordingly, it is desirable to periodically regenerate the catalyst by conventional techniques of carbon removal, such as treatment with an oxygen-containing gas, such as air. During such regeneration, it may also be desirable to use inert gas or steam dilution to control burn-off temperatures, as is also well known to those skilled in the art.

Following preparation of the catalytic composition, the catalyst may be prepared for use by purging with an inert gas, such at nitrogen. Normally, the catalyst would be disposed in the reactor and be brought up to reaction temperature by preheating with air, then purging with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher oxidation states of manganese and/or iron and, thereby, reduces initial carbon oxide formation.

With the exception of the temperature of operation, the operating conditions of the process, in accordance with the present invention, do not appear to be highly critical. Accordingly the following conditions of operation are those found effective and preferred.

When steam is used, the steam/hydrocarbon mol ratio may be between about 0.1/1 to about 10/1 and is preferably between about 0.5/1 and about 5/1.

The hydrocarbon gas hourly space velocity (GHSV) may range from about 100 to about 3000 but is preferably between about 500 and about 1000.

The operating pressure may be between about 0.1 and about 100 psia and is preferably beteen about 1 and about 60.

The temperature of operation appears to be significant in the conversion of feed hydrocarbons to olefins and particularly in improving the selectivity to ethylene. Suitable temperatures range between about 550° C. and about 850° C., with the preferred range being between about 650° C. and about 775° C.

The nature and advantages of the present invention are illustrated by the following example.

EXAMPLE

Quartz chips were utilized for a comparative run representative of thermal cracking in the presence of steam. All catalysts were prepared, in general, by the slurrying method previously described. For example, $Mg(OH)_2$ was added, as a solid, to a blending apparatus and the remaining components were added as aqueous solutions of metal salts, such as $Mn(NO_3)_2$ and $Cr(NO_3)_3.9H_2O$. The active components and promoting materials were in their oxide form but their concentrations are reported as weight percent of elemental metal based on the total weight of the catalyst.

The reactor was a fixed bed 18 mm (i.d.) quartz reactor which held 25 cc of catalyst. The reactor contained a quartz thermocouple well centered axially along the catalyst bed and the temperatures reported are the longitudinal midpoint in the catalyst bed.

In the experiments reported, all catalysts were pretreated in the same manner. This pretreatment involved air oxidation for 10 min., nitrogen purge for 2 min., hydrogen reduction for 10 min. and a final nitrogen purge. The catalyst was brought up to reaction temperature prior to the introduction of the hydrocarbon feed. The hydrocarbon feed was n-butane at a flow rate of 100 cc/min. through a water saturator at about 81° C., to produce a steam/feed hydrocarbon ratio of about 1/1. The combined feed plus steam flow rate resulted in approximately a 1 second residence time through the catalyst bed.

Effluent from the reactor was snap sampled and analyzed by chromatographic techniques. A reaction time of about 2-5 min. determines the "initial activity" of a catalyst. The conversion is reported as mol percent of n-butane converted. The reported selectivities are based on normalized mols of feed converted to the indicated products.

The results of this series of runs is reported in the following table.

TABLE

| Catalyst | Temp. °C. | Time Min. | Conv. | Selectivities $C_2=$ | $C_3=$ | $C_2$ | $\dfrac{C_2= + C_2}{C_3=}$ |
|---|---|---|---|---|---|---|---|
| 0.5% Cr/3% Ca/4% Mn/MgO | 711 | 3 | 76 | 41 | 15 | 25 | 4.40 |
|  | 702 | 7 | 52 | 40 | 21 | 20 | 2.86 |
|  | 710 | 20 | 55 | 35 | 29 | 16 | 1.76 |
|  | 711 | 35 | 55 | 33 | 32 | 15 | 1.50 |
|  | 710 | 45 | 56 | 30 | 34 | 13 | 1.26 |
|  | 707 | 60 | 55 | 30 | 34 | 13 | 1.26 |
|  | 710 | 80 | 58 | 28 | 36 | 12 | 1.11 |
| 3% Ca/4% Mn/MgO | 718 | 3 | 69 | 42 | 17 | 23 | 3.82 |
|  | 729 | 7 | 62 | 36 | 29 | 13 | 1.69 |
|  | 728 | 20 | 63 | 33 | 33 | 11 | 1.33 |
|  | 727 | 45 | 64 | 30 | 36 | 9 | 1.08 |
|  | 728 | 85 | 66 | 29 | 37 | 9 | 1.03 |
| Quartz Chips | 720 | 2–5 | 50 | 30 | 39 | 7 | 0.95 |
| 5% Cr/MgO | 678 | 2–5 | 50 | 28 | 36 | 10 | 1.06 |
| 5% Cr/CaO | 700 | 2–5 | 50 | 30 | 38 | 7 | 0.97 |
| 5% Cr/La$_2$O$_3$ | 698 | 2–5 | 50 | 20 | 28 | 8 | 1.00 |

The thermal cracking run (quartz chips) is typical and it is to be observed from this run that the ratio of ethylene plus ethane to propylene is near 1.00. Accordingly, significantly higher such ratios are clearly indicative of selectivity to ethylene and ethane, as opposed to propylene. Consequently, it is to be observed that substantially higher ethylene plus ethane/propylene ratios were obtained with both the Ca/Mn/MgO and the Cr/Ca/Mn/MgO catalysts. As a general guide, also, it is considered that the catalyst is to be "activated" when the propylene production equals or exceeds the ethylene production and particularly when the ratio of ethylene plus ethane/propylene approaches 1.00 (thermal conversion). On this basis it is to be seen that the catalysts containing chromium, as a promoter, were active for nearly an hour before the production of propylene significantly exceeded the production of ethylene and at 80 minutes on stream, without regeneration, this catalyst still produced a substantially higher ethylene plus ethane/propylene ratio than the thermal conversion. It is additionally observable that, while Ca/Mn/MgO is an excellent catalyst for the process of the present invention, this same catalyst containing a small amount of chromium oxide, as a promoter, selectively produced ethylene, as opposed to propylene, for at least twice the length of time that the catalyst without the chromium and the chromium oxide promoted catalyst was still highly effective for the production of ethylene plus ethane, as opposed to propylene, after 80 minutes, whereas the unpromoted catalyst began to approach thermal conversion after about 20 minutes.

The last three runs clearly indicate the ineffectiveness of combinations of chromium oxide and magnesium oxide, chromium oxide and calcium oxide and chromium oxide and lanthanum oxide. It has also been found that magnesium oxide, lanthanum oxide and cerium oxide alone result in essentially the same results as those obtained by the thermal steam cracking of n-butane in the presence of quartz chips.

While specific materials, conditions of operation, modes of operation and equipment have been referred to herein, is to be recognized that these and other specific recitals are for illustrative purposes and to set forth the best mode only and are not to be considered limiting.

What is claimed is:

1. A method for converting feed hydrocarbons comprising at least one of $C_3$ and $C_4$ hydrocarbons to less saturated hydrocarbons, comprising:

contacting said feed hydrocarbons with a catalyst composition selected from the group consisting of:

(a) a catalyst, consisting essentially of: about 0.1 to 30 wt. % of each of (1) at least one oxide of chromium and (2) at least one oxide of manganese and the balance of (3) at least one oxide of magnesium;

(b) a catalyst, comprising: about 0.1 to 30 wt. % of each of (1) at least one oxide of chromium and (2) at least one oxide of manganese and the balance of (3) at least one oxide of at least one metal selected from the group consisting of Lanthanum Series metals and niobium;

(c) a catalyst, consisting essentially of: about 0.1 to 30 wt. % of each of (1) at least one oxide of chromium, (2) at least one oxide of at least one metal selected from the group consisting of calcium, strontium, barium, tin, and antimony and (3) at least one oxide of manganese and the balance of (4) at least one oxide of magnesium; and (d) a catalyst, comprising: about 0.1 to 30 wt. % of each of (1) at least one oxide of chromium, (2) at least one oxide of at least one metal selected from the group consisting of calcium, strontium, barium, tin and antimony and (3) at least one oxide of manganese and the balance of (4) at least one oxide of at least one metal selected from the group consisting of Lanthanum Series metals and niobium, said wt. % being expressed in terms of the element based on the total weight of the catalyst, under conditions sufficient to convert said feed hydrocarbons to said less saturated product hydrocarbons.

2. A method in accordance with claim 1 wherein the catalyst composition comprises (1) at least one oxide of chromium, (2) at least one oxide of manganese and (3) at least one oxide of at least one metal selected from the group consisting of Lanthanum Series metals and niobium.

3. A method in accordance with claim 1 wherein the catalyst composition comprises: (1) at least one oxide of chromium, (2) at least one oxide of at least one metal selected from the group consisting of calcium, strontium, barium, tin and antimony, (3) at least one oxide of manganese and (4) at least one oxide of at least one metal selected from the group consisting of Lanthanum Series metals and niobium.

4. A method in accordance with claim 1 wherein the feed hydrocarbons comprise propane.

5. A method in accordance with claim 1 wherein the feed hydrocarbons comprise butanes.

6. A method in accordance with claim 1 wherein the feed hydrocarbons comprise a mixture of propane and butanes.

7. A method in accordance with claim 1 wherein the conditions are sufficient to selectively convert the feed hydrocarbons to ethylene and ethane.

8. A method in accordance with claim 7 wherein the conditions are sufficient to selectively convert the feed hydrocarbons to ethylene.

9. A method in accordance with claim 1 wherein the at least one metal selected from the group consisting of Lanthanum Series metals and niobium is at least one metal selected from the group consisting of Lanthanum Series metals.

10. A method in accordance with claim 9 wherein the at least one metal selected from the group consisting of Lanthanum Series metals is at least one metal selected from the group consisting of lanthanum and cerium.

11. A method in accordance with claim 1 wherein the catalyst composition consists essentially of (1) at least one oxide of chromium, (2) at least one oxide of manganese and (3) at least one oxide of magnesium.

12. A method in accordance with claim 1 wherein the catalyst composition consists essentially of (1) at least one oxide of chromium, (2) at least one oxide of at least one metal selected from the group consisting of calcium, strontium, barium, tin and antimony, (3) at least one oxide of manganese and (4) at least one oxide of magnesium.

13. A method in accordance with claim 1 wherein the temperature is maintained between about 550° to about 850° C.

14. A method in accordance with caim 1 wherein the method is carried out in the presence of steam at a steam/feed hydrocarbon ratio between about 0.1/1 and about 10/1.

15. A method in accordance with claim 1 wherein the sulfur content of the catalyst composition is below about 0.2 wt. %, expressed in terms of elemental sulfur based on the total weight of said catalyst.

16. A method for converting feed hydrocarbons comprising at least one of $C_3$ and $C_4$ hydrocarbons to less saturated hydrocarbons, comprising:

contacting said feed hydrocarbons, in the presence of steam, with a catalyst composition selected from the group consisting of:
(a) a catalyst composition, consisting essentially of: about 0.1 to 30 wt. % of each of (1) at least one oxide of chromium and (2) at least one oxide of iron and the balance of (3) at least one oxide of magnesium;
(b) a catalyst composition, comprising: about 0.1 to 30 wt. % of each (1) at least one oxide of chromium and (2) at least one oxide of iron and the balance of (3) at least one oxide of at least one metal selected from the group consisting of Lanthanum Series metals and niobium;
(c) a catalyst composition, consisting essentially of: about 0.1 to 30 wt. % of each (1) at least one oxide of chromium, (2) at least one oxide of iron and at least one oxide of manganese and the balance of (4) at least one oxide of magnesium, and
(d) a catalyst composition, comprising: about 0.1 to 30 wt. % of each (1) at least one oxide of chromium, (2) at least one oxide of iron and (3) at least one oxide of manganese and the balance of (4) at least one oxide of at least one metal selected from the group consisting of Lanthanum Series metals and niobium, said wt. % being expressed in terms of the element based on the total weight of the catalyst, under conditions sufficient to convert said feed hydrocarbons to said less saturated hydrocarbons.

17. A method in accordance with claim 16 wherein the catalyst composition consists essentially of: (1) at least one oxide of chromium, (2) at least one oxide of iron, (3) at least one oxide of manganese and (4) at leaat one oxide of magnesium.

18. A method in accordance with claim 16 wherein the catalyst composition comprises: (1) at least one oxide of chromium, (2) at least one oxide of iron and (3) at least one oxide of at least one metal selected from the group consisting of Lanthanum Series metals and niobium.

19. A method in accordance with claim 16 wherein the feed hydrocarbons comprise propane.

20. A method in accordance with claim 16 wherein the feed hydrocarbons comprise butanes.

21. A method in accordance with claim 16 wherein the feed hydrocarbons comprise a mixture of propane and butanes.

22. A method in accordance with claim 16 wherein the conditions are sufficient to selectively convert the feed hydrocarbons to ethylene and ethane.

23. A method in accordance with claim 22 wherein the conditions are sufficient to selectively convert the feed hydrocarbons to ethylene.

24. A method in accordance with claim 16 wherein the at least one metal selected from the group consisting of Lanthanum Series metals and niobium is at least one metal selected from the group consisting of Lanthanum Series metals.

25. A method in accordance with claim 24 wherein the at least one metal selected from the group consisting of Lanthanum Series metals is at least one metal selected from the group consisting of lanthanum and cerium.

26. A method in accordance with claim 16 wherein the catalyst composition consists essentially of (1) at least one oxide of chromium, (2) at least one oxide of iron and (3) at least one oxide of magnesium.

27. A method in accordance with claim 16 wherein the catalyst composition comprises (1) at least one oxide of chromium (2) at least one oxide of iron, (3) at least one oxide of manganese and (4) at least one oxide of at least one metal selected from the group consisting of Lanthanum Series metals and niobium.

28. A method in accordance with claim 16 wherein the temperature is maintained between about 550° C. and about 850° C.

29. A method in accordance with claim 16 wherein the steam/feed hydrocarbon ratio is maintained between about 0.1/1 and 10/1.

30. A method in accordance with claim 16 wherein the sulfur content of catalyst compositions is below about 0.2 wt. %, expressed in terms of elemental sulfur based on the total weight of said catalyst.

* * * * *